United States Patent [19]

Lum et al.

[11] Patent Number: 5,509,418
[45] Date of Patent: Apr. 23, 1996

[54] ULTRASOUND DIAGNOSTIC PROBE HAVING ACOUSTICALLY DRIVEN TURBIN

[75] Inventors: Paul Lum; Michael Greenstein, both of Los Altos; Edward Verdonk, Redwood City, all of Calif.

[73] Assignee: Hewlett-Packard Co., Palo Alto, Calif.

[21] Appl. No.: 373,682

[22] Filed: Jan. 17, 1995

[51] Int. Cl.$^6$ ..................................................... A61B 8/12
[52] U.S. Cl. ..................................................... 128/662.06
[58] Field of Search ............................ 128/660.03, 660.1, 128/662.03–662.06; 310/334; 333/149

[56] References Cited

U.S. PATENT DOCUMENTS

| | | | |
|---|---|---|---|
| 4,794,931 | 1/1989 | Yock | 128/662.06 |
| 5,000,185 | 3/1991 | Yock | 128/662.06 |
| 5,059,851 | 10/1991 | Corl et al. | 310/334 |
| 5,176,141 | 1/1993 | Bom et al. | 128/662.06 |
| 5,217,018 | 6/1993 | Dias | 128/662.06 |
| 5,240,003 | 8/1993 | Lancee et al. | 128/662.06 |
| 5,271,402 | 12/1993 | Yeung et al. | 128/660.1 |
| 5,284,148 | 2/1994 | Dias et al. | 128/662.06 |
| 5,371,483 | 12/1994 | Bhordwaj | 333/149 |
| 5,429,136 | 7/1995 | Milo et al. | 128/662.06 X |

*Primary Examiner*—Francis Jaworski

[57] ABSTRACT

A catheter apparatus for obtaining an image of internal surface characteristics of a vascular vessel is provided. The catheter apparatus comprises an tubular element adapted for insertion into the vascular vessel, a non-rotating acoustic waveguide disposed within the tubular element and coupled to a source of an ultrasonic signal located external to the vascular vessel, and an acoustically driven turbine. The turbine is responsive to the ultrasonic signal for directing the ultrasonic signal in a rotating pattern from a distal end of the acoustic waveguide through the tubular element at an angle relative to an axis of the vascular vessel. The ultrasonic signal includes a low frequency ultrasonic signal and a high frequency ultrasonic signal. The low frequency ultrasonic signal drives the acoustically driven turbine to direct the high frequency ultrasonic signal in the rotating pattern. The acoustically driven turbine comprises a plurality of turbine blades, and either an acoustic reflecting surface or an acoustic refracting lens. At least one transducer disposed external to the vascular vessel provides the source of the high and the low frequency ultrasonic signals. The tubular element may further be provided with a lumen for carrying a guidewire.

20 Claims, 7 Drawing Sheets

FIG. 9C ular ultrasonic imaging, and more particularly, to a catheter having an acoustically driven turbine that rotates an ultrasonic beam continuously through an area of interest within a vascular vessel.

ULTRASOUND DIAGNOSTIC PROBE HAVING ACOUSTICALLY DRIVEN TURBIN

RELATED APPLICATION

This invention relates to copending application Ser. No. 08/373,676, filed on the same date herewith, entitled ULTRASOUND DIAGNOSTIC PROBE HAVING NON-ROTATING ACOUSTIC WAVEGUIDE, filed in the name of the inventors herein, and owned by the assignee of this application.

BACKGROUND OF THE INVENTION

1. Field of the Invention

This invention relates to catheter systems for intravascular ultrasonic imaging, and more particularly, to a catheter having an acoustically driven turbine that rotates an ultrasonic beam continuously through an area of interest within a vascular vessel.

2. Description of Related Art

Ultrasonic imaging systems are increasingly desirable for use in catheter-based probes to produce high definition images of internal surface characteristics of a blood vessel of a human body. Catheter-based probes typically comprise a flexible tubular element that is adapted to be inserted into a blood vessel in the vascular system. For example, such a probe may be inserted into the femoral artery of a patient in order to examine the coronary vessels and identify any stenosis or occlusion present within the vessels. This procedure can avoid the need for more invasive diagnostic techniques which might increase the risk to the patient and the associated recovery time. Catheter-based ultrasonic imaging is also known to improve the effectiveness of interventional therapies, such as angioplasty, atherectomy, laser ablation, and drug delivery, by enabling such therapies to be specifically directed where they will be most effective, and to evaluate the outcome of such therapy.

The ultrasonic imaging systems of these catheters typically comprise a piezoelectric transducer that generates an ultrasonic signal in response to an external electrical excitation. The ultrasonic signal is directed to an area of interest within a vessel, where it propagates through the blood until it reaches the interior surface of the vessel. Reflections of the signal, or echoes, return to the piezoelectric transducer, which converts these echoes to corresponding electrical signals. The electrical signals are then collected, processed and displayed as a two-dimensional image on a CRT screen.

In order to obtain a complete image of the interior surface area of the vessel, it is necessary to sweep the ultrasonic signal in a pattern about an axis of the vessel. Various techniques have been proposed to sweep the ultrasonic signal in the desired pattern which include the placement of the piezoelectric transducer in the distal end of the catheter. The transducer may be rotated directly to sweep the ultrasonic signal in the desired pattern, or the transducer may be fixed within the catheter and a reflective surface rotated to sweep the ultrasonic signal in the desired pattern. See U.S. Pat. No. 5,000,185, issued to Yock, for METHOD FOR INTRAVASCULAR TWO-DIMENSIONAL ULTRA-SONOGRAPHY AND RECANALIZATION. In this reference, torque for the rotation is provided by an external motor connected through the catheter by a torque cable to either the transducer or the reflective surface. Alternatively, a fluid coupled turbine may be disposed in the distal end of the catheter to provide the rotational torque. See U.S. Pat. No. 5,271,402, issued to Yeung et al., for TURBINE DRIVE MECHANISM FOR STEERING ULTRASOUND SIGNALS. In yet another alternative technique, a micro-motor may be disposed in the distal end of the catheter to provide the rotational torque. See U.S. Pat. No. 5,176,141, issued to Bom et al., for DISPOSABLE INTRA-LUMINAL ULTRASONIC INSTRUMENT.

There are numerous disadvantages associated with placing the piezoelectric transducer in the distal end of the catheter. The transducer may emit leakage currents inside the patient that can induce fibrillation when the probe images a coronary artery. Electrical wires that connect the transducer to external circuitry inherently act as antennas and receive radio frequency (RF) interference present within the environment of the catheterization laboratory. This RF interference may appear as noise in the electrical signals travelling to and from the transducer which distorts the two-dimensional image.

Another disadvantage of placing the transducer at the distal end of the catheter is that it increases the difficulty of varying the frequency of the ultrasonic signal. The piezoelectric transducer has a frequency of operation determined by its thickness. It may be desirable for the probe operator to adjust the transducer frequency in order to obtain a more precise image resolution or to illuminate a particular region of interest within the vessel. The transducer thickness is limited by the rather confined space within the distal end of the catheter, and the transducer cannot be easily replaced during catheterization.

Yet another disadvantage of placing the transducer at the distal end of the catheter is its associated expense. The catheter is typically discarded after a single use in order to prevent the transmission of disease. The transducer is costly to manufacture, and its disposal increases the already high cost of probe-catheterization techniques. Moreover, the higher resolution transducers are among the most expensive to manufacture, which tends to discourage use of such transducers in favor of less desirable imaging systems.

An alternative approach to these prior art techniques is to dispose the piezoelectric transducer external to the patient, and to direct the ultrasonic signal into the catheter by use of an acoustic waveguide. To sweep the ultrasonic signal in the desired pattern, the entire acoustic waveguide is rotated by an external device, such as a motor. See U.S. Pat. No. 5,284,148, issued to Dias et al., for INTRACAVITY ULTRASOUND DIAGNOSTIC PROBE USING FIBER ACOUSTIC WAVEGUIDES. This approach substantially minimizes the disposable elements of the catheter, and provides greater flexibility to the operator in terms of transducer selection.

Nevertheless, spinning waveguide imaging systems have substantial drawbacks as well. First of all, rotation of the acoustic waveguide subjects the relatively delicate waveguide to undesirable mechanical stress which could potentially damage the waveguide or reduce its acoustic conductivity. Second, the spinning waveguide is susceptible to non-uniform rotational velocity due to frictional binding of the waveguide by contact with the catheter sidewall. The frictional binding is generally most severe when the probe operator is attempting to steer the catheter through a sharp turn, such as from the aorta to the entry into the coronary vessel, or other so-called "torturous turns" within the vascular system. At the turning point, the spinning waveguide is pinched slightly which causes the overall rotational rate of the waveguide to decrease momentarily. The decrease in rotational rate may also be followed by a slight increase in the rotational rate due to an energy release caused by the sudden un-binding of the waveguide. The fluctuations of the rotational rate of the spinning waveguide can result in undesirable distortion of the two-dimensional image. The spinning torque cable imaging catheters described above are also prone to such non-rotational velocity effects.

Accordingly, it would be desirable to provide a catheter-based ultrasonic imaging system capable of sweeping an ultrasonic signal in a pattern about an axis of the blood vessel, which overcomes the numerous disadvantages of the prior art.

SUMMARY OF THE INVENTION

In accordance with the teachings of this invention, a catheter apparatus for obtaining an image of a vascular vessel is provided. The catheter apparatus comprises a tubular element adapted for insertion into the vascular vessel, a non-rotating acoustic waveguide disposed within the tubular element coupled to a source of an ultrasonic signal located external to the vascular vessel, and an acoustically driven turbine responsive to the ultrasonic signal for directing the ultrasonic signal in a rotating pattern from a distal end of the acoustic waveguide through a distal end of the tubular element. The ultrasonic signal may be directed from the distal end of the tubular element at an angle ranging between 10° and 90° relative to an axis of said vascular vessel.

In particular, the ultrasonic signal comprises a low frequency ultrasonic signal and a high frequency ultrasonic signal. The low frequency ultrasonic signal drives the acoustically driven turbine to rotate and direct the high frequency ultrasonic signal in the rotating pattern. The acoustically driven turbine comprises a plurality of turbine blades, and has either an acoustic reflecting surface or an acoustic refracting lens. The source of the high and low frequency ultrasonic signals comprises at least one transducer disposed external to the vascular vessel.

A more complete understanding of the non-rotating acoustic imaging waveguide will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

This invention provides a catheter-based ultrasonic imaging system capable of sweeping an ultrasonic signal in a rotating pattern about an axis of a blood vessel. In general, the invention provides a catheter apparatus having a non-rotating acoustic waveguide and a rotating acoustically driven turbine that has either a reflective or refractive element that directs an ultrasonic signal in a desired pattern within the blood vessel.

Figure 1:
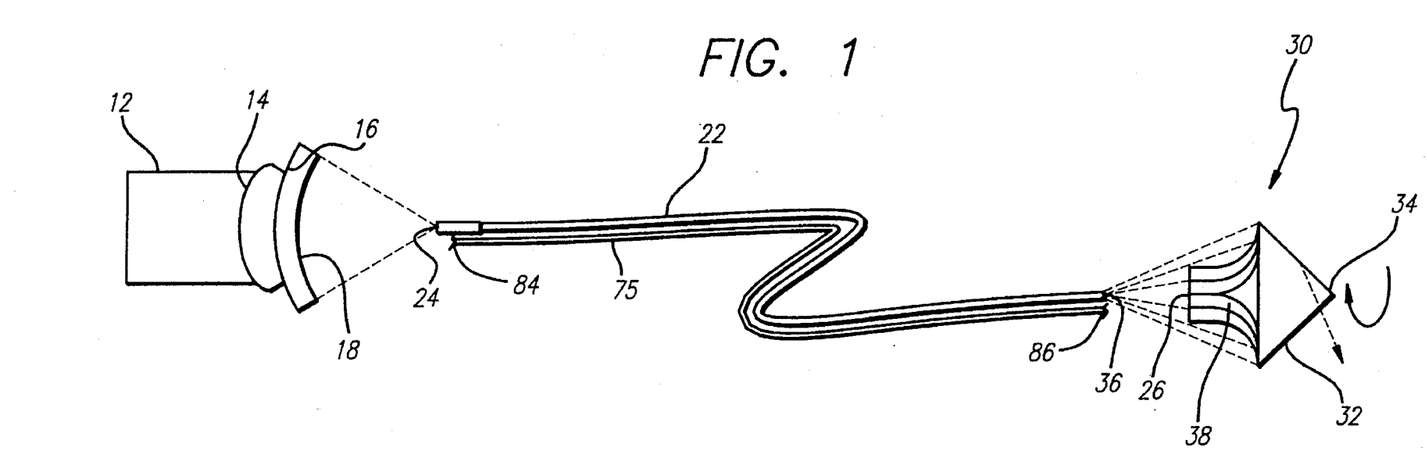
FIG. 1 is a side perspective view of a non-rotating acoustic waveguide having low and high acoustic transducers at a proximal end and an acoustically driven turbine at a distal end.

General operation of the catheter apparatus of the present invention will first be described with reference to FIG. 1 illustrating a side perspective view of a non-rotating acoustic waveguide for use in an ultrasound diagnostic probe. The acoustic waveguide 22 extends the length of the catheter-based system, and is used to conduct an acoustic signal between its proximal end 24 and its distal end 36. As known in the art, the acoustic waveguide 22 is similar to an optical waveguide, i.e., optical fiber. Both acoustic waveguides and optical waveguides typically comprise a central core and an outer cladding which surrounds the core and is in intimate acoustic contact with the core. The purpose of the cladding is to keep the acoustic signals within the core. Ideally, the waveguide guides the acoustic signals which reflect off the cladding and remain within the core. It is anticipated that the acoustic waveguide 22 be comprised of a glass material having generally high flexibility.

The catheter apparatus may further include a guidewire 75 that extends the length of the acoustic waveguide 22. The guidewire 75 has a proximal end 84 that extends beyond the proximal end 24 of the waveguide 22. The guidewire 75 also has a distal end 86 that may be coextensive with the distal end 36 of the acoustic waveguide or may extend beyond the distal end of the acoustic waveguide, as will be further described below. As known in the art, the guidewire 75 enables the operator of the catheter apparatus to steer the distal end of the catheter as it travels through the vessel.

Disposed at the proximal end 24 of the acoustic waveguide 22 are a low frequency piezoelectric transducer 14, a high frequency piezoelectric transducer 16, and a transducer backing layer 12. Both the low frequency and high frequency piezoelectric transducers 14, 16 are spherically shaped having convex and concave surfaces. The transducers 14, 16 are comprised of a crystalline material that is machined to a desired thickness and radius of curvature. As known in the art, the thickness of a transducer governs the frequency of an output acoustic signal of the transducer, and a radius of curvature of the transducer governs its focal point. The transducers 14, 16 may be formed from a common structure, or alternatively, may be formed separately and combined together in a nested manner. The convex and concave surfaces of the piezoelectric transducers may be further metallized with chromium and/or gold films so as to improve the acoustic generating capabilities of the transducers.

The proximal end 24 of the acoustic waveguide 22 is located at the focal point of the high frequency transducer 16 and faces a concave surface 18 of the transducer. Electrical signals drive the low frequency piezoelectric transducer 14 so that it generates emitted acoustic signals that have a frequency in the ultrasonic range between 100 KHz and 1 MHz, and the high frequency piezoelectric transducer 16 in the ultrasonic range between 10 MHz and 50 MHz. As known in the art, the transducers 14, 16 produce acoustic signals at both the concave surfaces and convex surfaces, and the backing layer 12 has an acoustic impedance matched to the transducers to absorb the acoustic signals from the respective convex surfaces. The acoustic signals from the concave surface 18 are coupled into the proximal end 24 of the waveguide 22, and are transmitted through the waveguide to its distal end 36.

Figure 10:
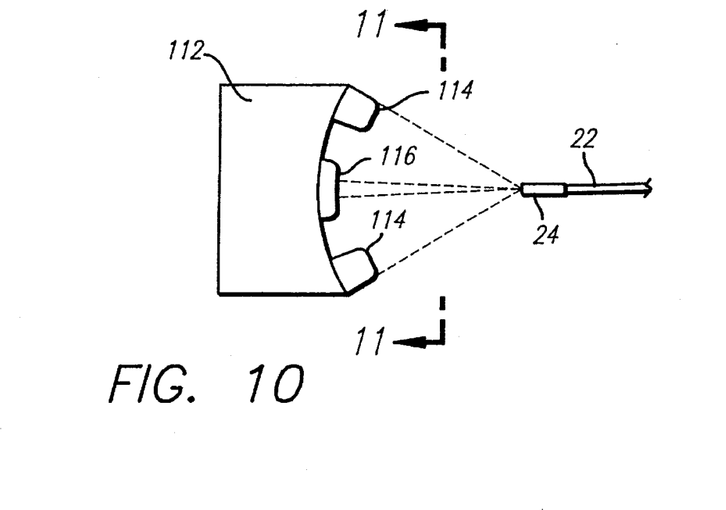
FIG. 10 is a side view of an alternative embodiment of the high and low frequency transducers of FIG. 1.
Figure 11:
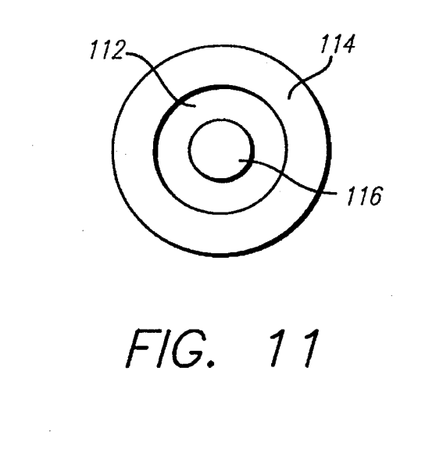
FIG. 11 is an end sectional view of the high and low frequency transducers, as taken through the section 11—11 of FIG. 10.

FIGS. 10 and 11 illustrate an alternative embodiment of the proximal end of the catheter apparatus. Instead of using a nested structure for the low and high frequency piezoelectric transducers 14, 16 as in FIG. 1, the transducers are separately disposed on a backing layer 112. A high frequency piezoelectric transducer 116 is spherically-shaped and centrally disposed on the backing layer 112. A low frequency piezoelectric transducer 114 is ring-shaped with a spherical cross-section and is concentrically disposed around the high frequency piezoelectric transducer 116 with a space provided therebetween. Both the low frequency and high frequency transducers 114,116 share a common focal point that coincides with the proximal end 24 of the acoustic waveguide 22. The low frequency transducer 114 has a greater thickness than the high frequency transducer 116, and may be formed from a common initial structure from which the transducers are machined to respective desired thicknesses. The low and high frequency transducers 114, 116 are electrically driven as described above with respect to FIG. 1.

Returning to FIG. 1, a turbine 30 is provided at the distal end 36 of the acoustic waveguide 22. The turbine 30 comprises a receiving surface 26, a concave rear surface 38, and a cone-shaped forward surface 32. The forward surface 32 has an apex 34. It is anticipated that the turbine 30 be comprised of an acoustically conductive material. The turbine 30 has an axis of symmetry that is coextensive with an axis of the catheter. As will be described in greater detail below, low frequency acoustic signals provided by the low frequency transducer 14 cause the turbine to rotate about its axis, and high frequency acoustic signals provided by the high frequency transducer 16 pass through the turbine and are either reflected or refracted outwardly into the vessel. As the turbine rotates, the high frequency signals are swept in a rotating pattern to enable the entire interior surface of the vessel to be imaged.

An acoustic coupling fluid may be utilized in the space between the transducers 14, 16 and the proximal end 24 of the acoustic waveguide 22 to couple the acoustic signals between the transducers and the acoustic waveguide. Similarly, an acoustic coupling fluid may be utilized in the space between the distal end 36 of the acoustic waveguide 22 and the receiving surface 26 of the turbine 30. It is anticipated that acoustic impedance matching layers on the transducers 14, 16, on both ends of the acoustic waveguide 22, and on the receiving surface 26 will provide efficient conduction of acoustic signals between both the transducers and the proximal end of the waveguide as well as between the distal end 36 of the waveguide 22 and the turbine 30.

Figure 2:
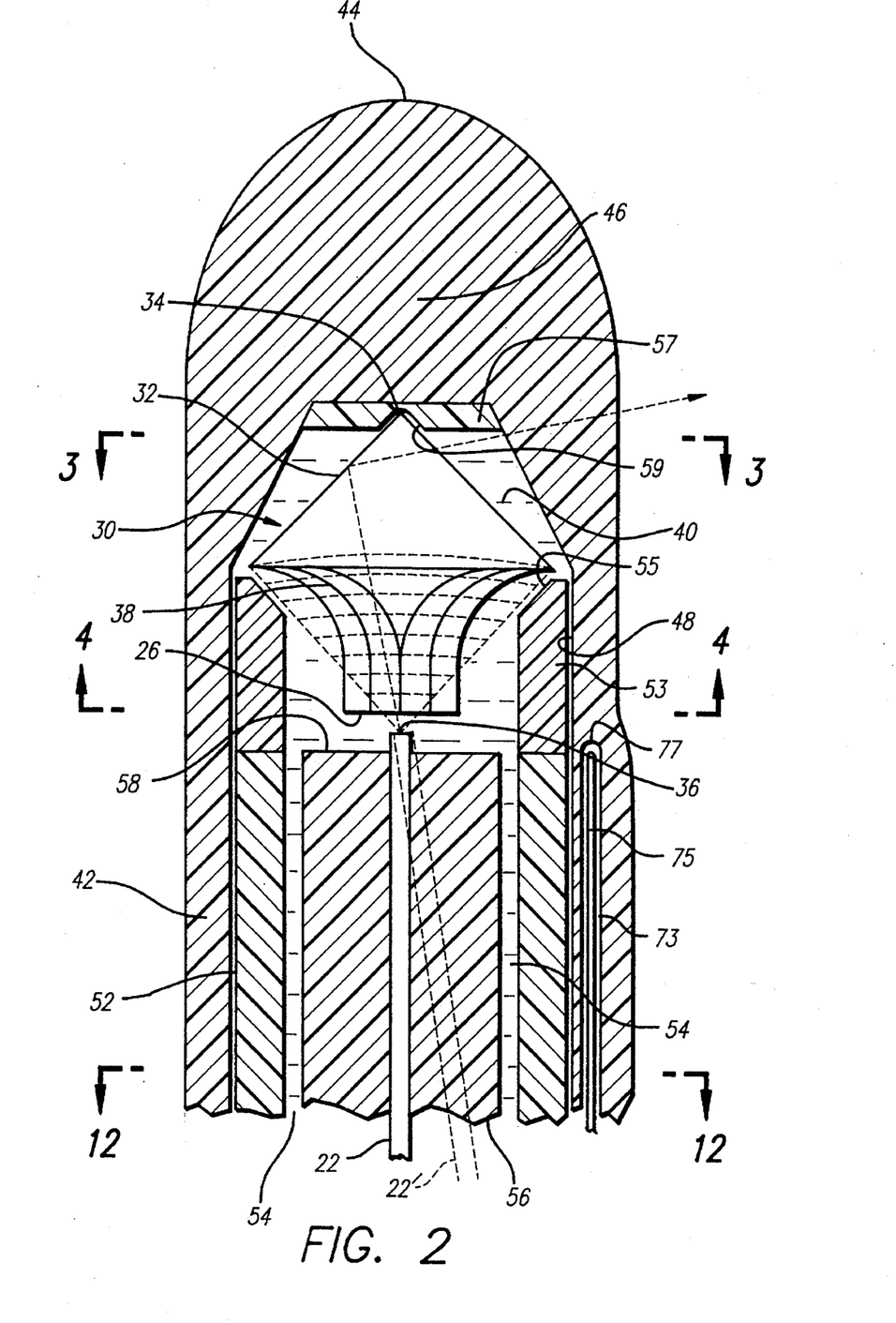
FIG. 2 is a side sectional view of the distal end of an intracavity ultrasound diagnostic probe having the non-rotating acoustic waveguide and acoustically driven turbine of FIG. 1.

Referring now to FIG. 2, a distal end of a catheter of the present invention is illustrated in greater detail. The catheter is adapted for insertion into a blood vessel in the vascular system of a human body. The catheter comprises an elongated outer tubular element 42 having a generally rounded tip 44. The outer tubular element 42 may be formed as a single extrusion of a flexible plastic material, such as polystyrene, polypropylene or other type of plastic. The outer tubular element 42 necessarily provides a smooth surface that can be readily inserted into the blood vessel without undesired friction. It is further desirable that the outer tubular element 42 be comprised a substantially acoustically transparent material to allow an ultrasonic signal to be transmitted therethrough. Alternatively, an acoustically transparent window can be provided in the region of the distal end of the catheter.

The outer tubular element 42 has an inner surface 48 that defines an interior chamber 40. The turbine 30 is located within the chamber 40, and is generally suspended within coupling fluid contained within the chamber. The turbine 30 is configured with the apex 34 pointing in the direction of the tip 44, and the receiving surface 36 facing in the direction of the proximal end of the catheter. The outer tubular element 42 has a solid nose portion 46 between the distal end 44 and the chamber 40 that acts as an acoustic lens for focusing the acoustic signals from the turbine 30 into the interior of the vascular vessel. It should be apparent that the nose portion 46 can be selectively shaped to provide desired half angles, beam widths or other pertinent characteristics for the acoustic signal.

Figure 12:
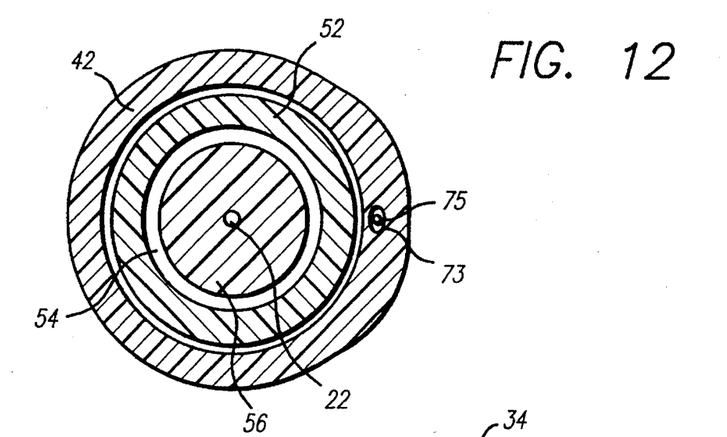
FIG. 12 is an end sectional view of the distal end of the ultrasound diagnostic probe, as taken through the sections 12—12 of FIGS. 2 and 5.

The outer tubular element 42 may additionally comprise a lumen 73 causing an outer surface of the outer tubular element to protrude slightly outward, as further illustrated in FIG. 12. The lumen 73 carries the guidewire 75 that extends the length of the catheter apparatus to an end point 77 prior to the distal end of the outer tubular element. The guidewire 75 does not extend all the way to the distal end of the outer tubular element 42, otherwise the guidewire may interfere with ultrasonic imaging operations.

The chamber 40 is enclosed at an end opposite from the nose portion 46 by a plug 56. An end surface 58 of the plug 56 forms an interior wall of the chamber 40. The plug 56 has an outside surface 52 having a diameter that is slightly smaller than an inside diameter of the tubular element 42, so that the plug can be readily inserted into the tubular element and provide a friction fit therebetween.

A retaining ring 53 extends axially from the end surface 58 at an outside diameter portion thereof in the direction of the tip 44. The retaining ring 53 has a tapered inner surface 55 that provides a guide surface for the turbine 30. In addition, a guide disk 57 having a dimple 59 is disposed at a distal end of the chamber 40, with the apex 34 of the turbine 30 extending into the dimple. Though the turbine 30 is not fixed in position within the chamber 40, it is constrained from undesired turning within the chamber in a direction substantially off its axis by the particular shape of the chamber 40, including the tapered inner surface 55 and the dimple 59. Once the turbine 30 rotates in response to the low frequency signal, the turbine tends to align itself with the axis.

The plug 56 further has a central bore that permits the waveguide 22 to be inserted therethrough. This way, the waveguide 22 is substantially fixed in position with its distal end 36 in a proper orientation with respect to the receiving surface 26 of the turbine 30. The bore through the plug 56 may be substantially axial in direction so that the distal end 36 of the waveguide 22 is oriented along an axis of the turbine 30, or alternatively, the bore can be disposed off-axis with the waveguide oriented accordingly, such as illustrated at 22'. The plug 56 may further contain one or more flow channels 54 that direct coupling fluid to and from the chamber 40. It is anticipated that the plug 56 extend only a relatively short distance from the distal end of the catheter, and not an entire length of the catheter, in order to maintain maximum flexibility of the catheter.

Figure 3:
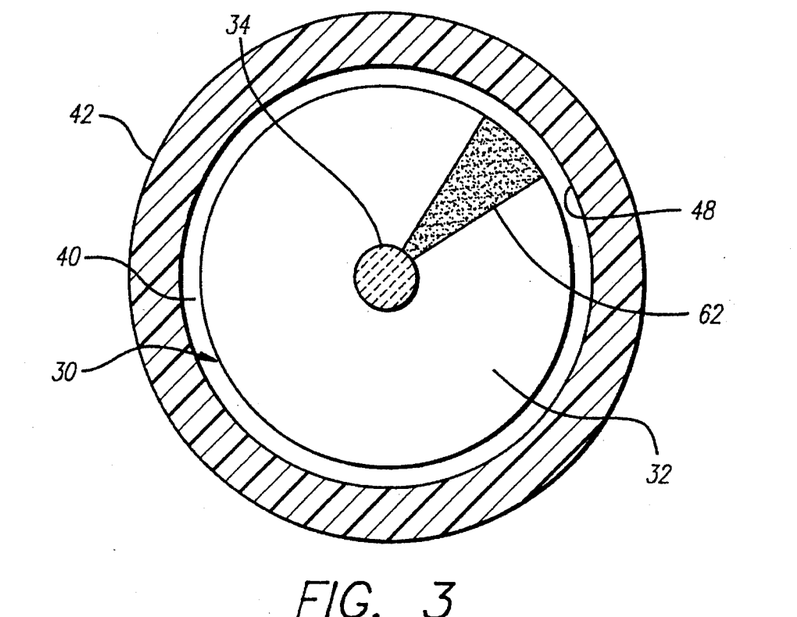
FIG. 3 is an end view of the acoustically driven turbine as taken through the section 3—3 of FIG. 2.
Figure 4:
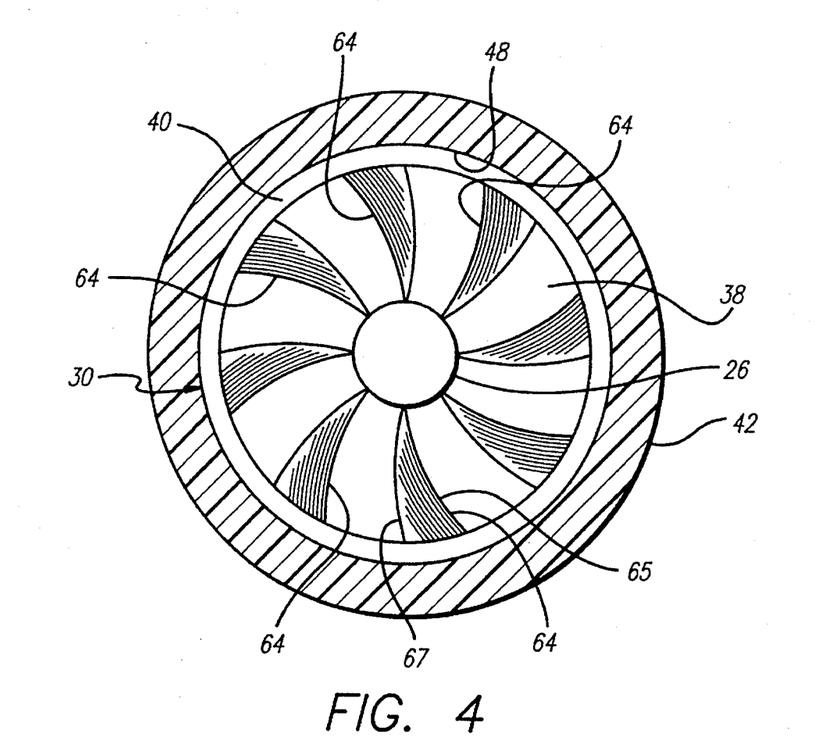
FIG. 4 is an opposite end view of the acoustically driven turbine as taken through the section 4—4 of FIG. 2.

Referring now to FIGS. 3 and 4, the turbine 30 is illustrated in greater detail. FIG. 3 shows a first end view of the turbine 30 disposed within the chamber 40 defined by the inner surface 48 of the tubular element 42. The forward surface 32 of the turbine 30 includes a transmitting element 62 defined in a pie-shaped portion thereof. The transmitting element 62 provides reflection of an acoustic signal coupled from the waveguide 22 into the turbine 30. The transmitting element 62 may have a surface characteristic that differs from the rest of the forward surface 32 such as provided by selective etching or other micro-machining process. Alternatively, the turbine 30 may be comprised of a distinct type of material disposed at the transmitting element 62 that alters its acoustic conducting properties. Fabrication of the turbine 30 is described in greater detail below.

FIG. 4 illustrates a second end view of the turbine 30 with the receiving portion 26 substantially centered on a central axis of the turbine. A plurality of turbine blades 64 are provided on the rear surface 38. Each of the turbine blades 64 are formed on the rear surface 38 of the turbine 30 by selective machining or etching to a desired depth, so that a trailing edge 65 is provided to a substantially shallower depth than a leading edge 67 thereof. The shape, depth, and number of individual turbine blades 64 can be selected in order to achieve a desired rotation rate for the turbine 30.

Figure 5:
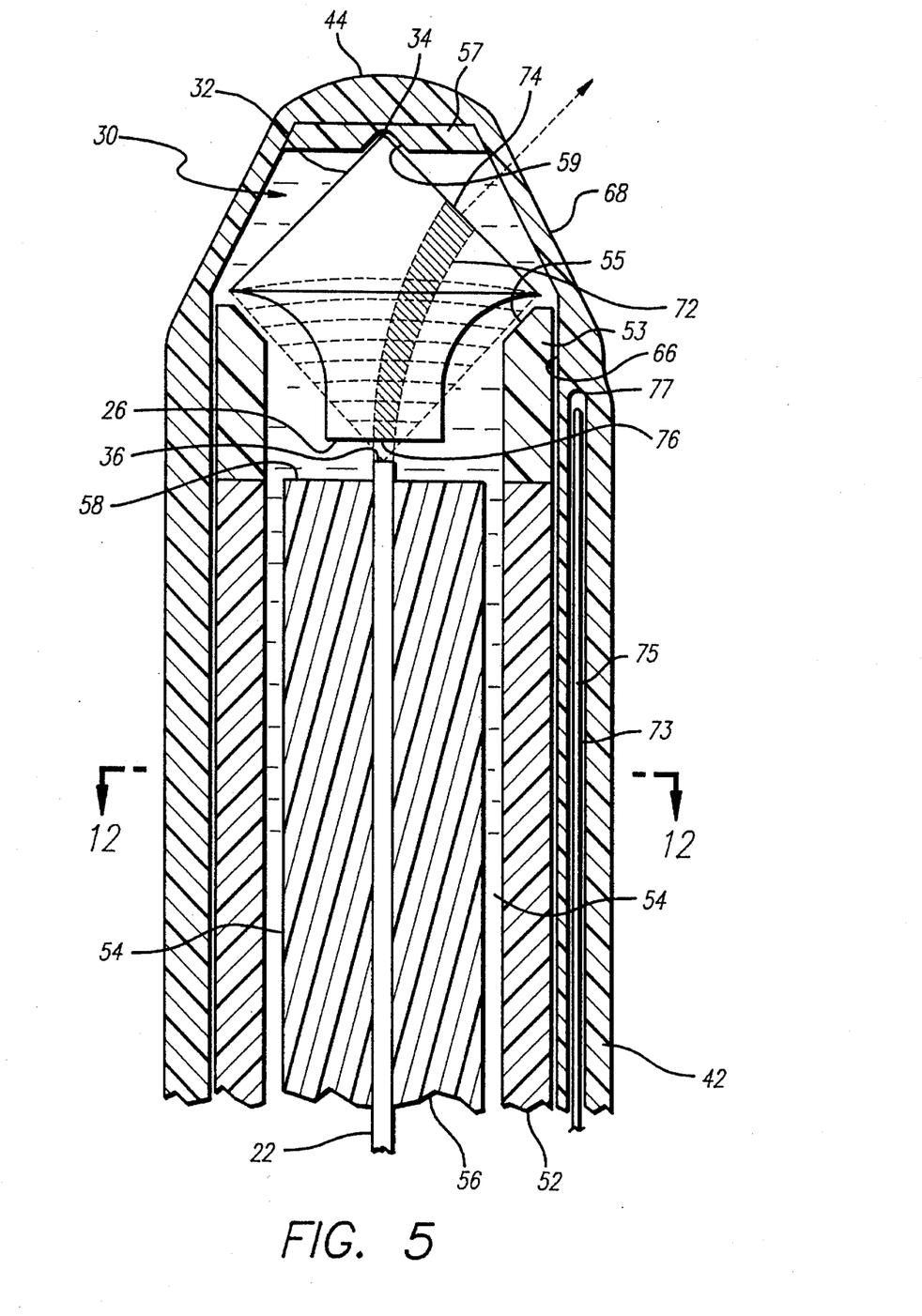
FIG. 5 is a side sectional view of an alternative embodiment of the distal end of an intracavity ultrasound diagnostic probe.

An alternative embodiment of a distal end of a catheter of the present invention is illustrated in FIG. 5. Like reference numerals are used to describe like elements of the catheter of FIG. 2. The alternative embodiment of FIG. 5 differs from the embodiment of FIG. 2 in that a refractive transmitting element 72 is provided within the turbine 30. The transmitting element 72 has a curved funnel shape with a first end 76 terminating at the receiving surface 26 of the turbine, and a second end 74 terminating at a portion of the conic portion 32. The transmitting element 72 may be comprised of an acoustically refractive material that channels high frequency acoustic waves from the first end 76 to the second end 74. In this embodiment, the tubular element 42 of the catheter may narrow sharply at the tip 44 with angled portions 68 providing a transparent acoustic window for the acoustic energy transmitted from the turbine. As in the tubular element 42 of FIG. 2, the tubular element may comprise a lumen 73 that carries a guidewire 75. The guidewire 75 may extend closer to the tip 44 in this alternative embodiment than in the previous embodiment since the ultrasonic signal transmitted by the turbine 30 is generally more forward directed.

Figure 6:
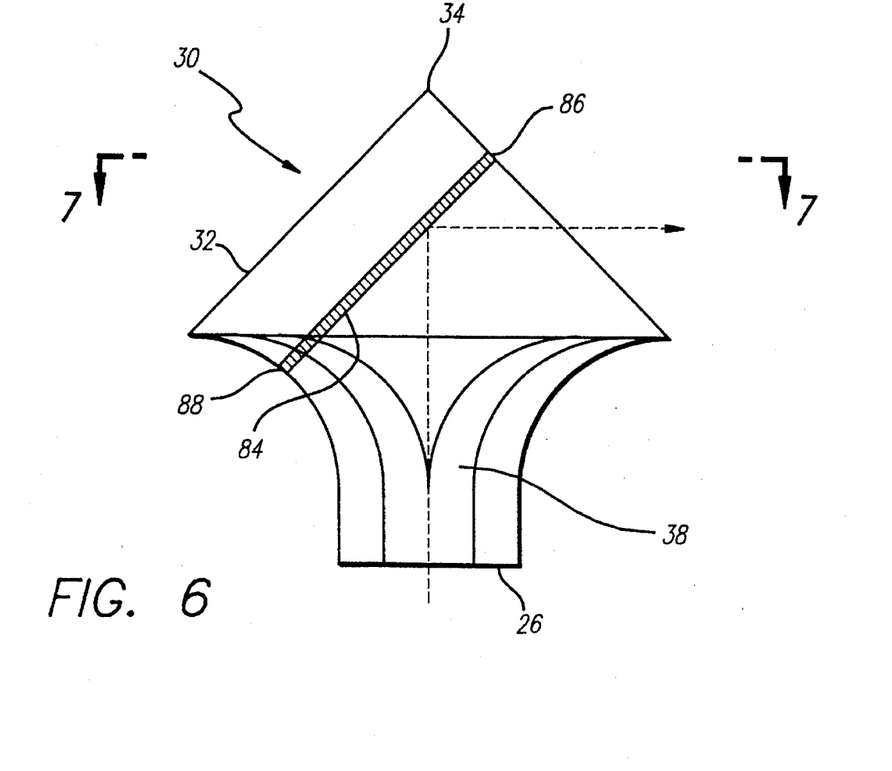
FIG. 6 is a side sectional view of an embodiment of the acoustically driven turbine.
Figure 7:
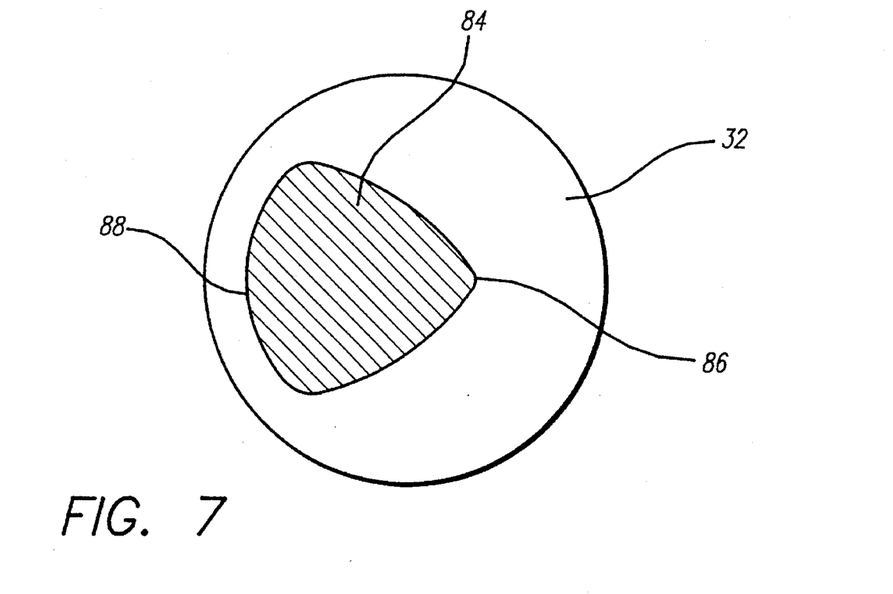
FIG. 7 is an end sectional view of the embodiment of the acoustically driven turbine as taken through the section 7—7 of FIG. 6.
Figure 8:
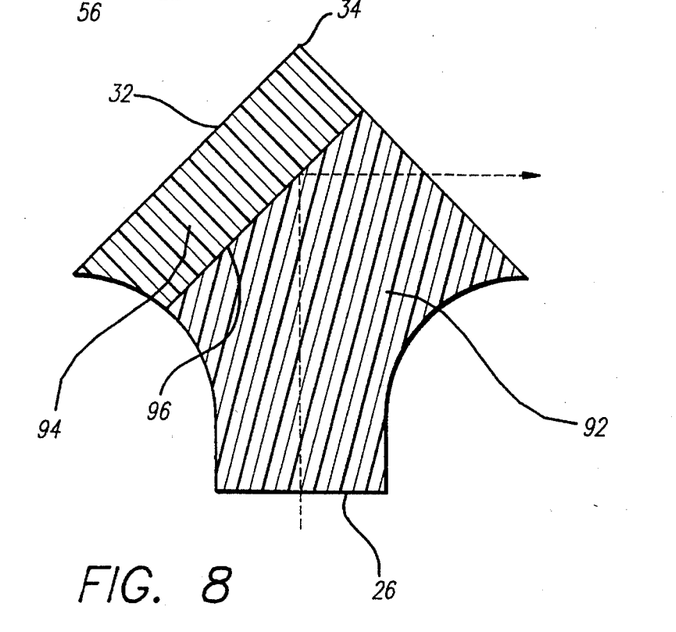
FIG. 8 is a side sectional view of another embodiment of the acoustically driven turbine.

Fabrication of the turbine 30 is illustrated in greater detail in FIGS. 6 through 8. FIGS. 6 and 7 illustrate a turbine 30 having a reflective member 84 embedded therein. The reflective member 84 may be formed of an acoustically reflective material, such as metal. To fabricate the turbine 30, the reflective element 84 may first be embedded in a solid block of acoustic conductive material. The block would then be formed into the desired shape, such as by selective etching or micro-machining processes. A first edge 86 of the reflective element 84 would coincide with the cone-shaped forward surface 32, and a second edge 88 of the reflective element would terminate at the rear surface 38 of the turbine. The orientation angle of the reflective element 84 within the turbine 30 can be selected to provide a desired reflective pattern for the acoustic signal.

Alternatively, as illustrated in FIG. 8 the turbine 30 can be comprised of a composite of two separate types of acoustically conductive material. The two portions 92, 94 can be bonded together into an initial block, and formed into a desired shape as set forth above. Acoustic signals transmitted through the turbine will reflect at the boundary 96 defined between the disparate portions of material 92, 94.

Operation of the turbine 30 will now be described with reference to FIGS. 1 and 9A–9C, which illustrates ultrasonic pulse time versus amplitude. The turbine 30 has three distinct modes of operation. In a first mode of operation, illustrated in FIG. 9A, the turbine 30 is brought from a non-rotating state to a full rotational speed. Low frequency acoustic pulses are provided by the low frequency transducer 14, which cause an acoustic pressure on the receiving surface 26 and the rear surface 38 of the turbine 30. This acoustic pressure causes the turbine 30 to rotate. The rotation rate of the turbine can be controlled by varying the width of the acoustic pulses (b), or by varying the space between adjacent acoustic pulses (a), known as pulse width modulation.

Figure 9A:
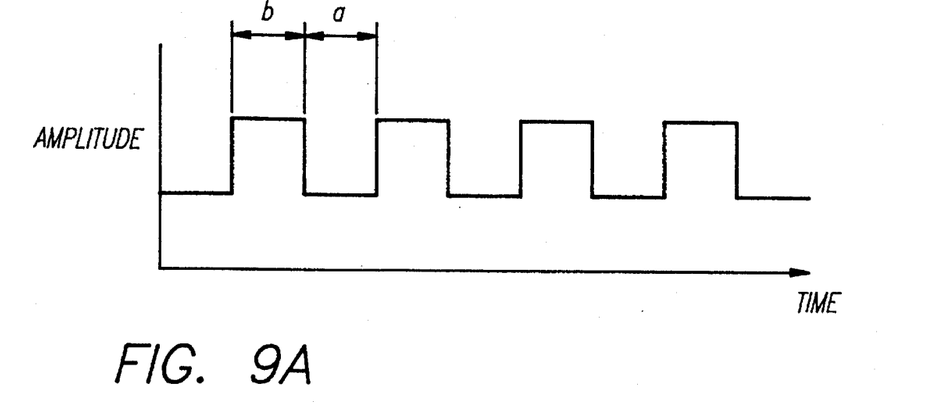
FIGS. 9A–9C illustrate respectively the acoustic pulse characteristics for a spin-up phase, an imaging phase, and a steady-state phase of operation for the intracavity ultrasound diagnostic probe.
Figure 9B:
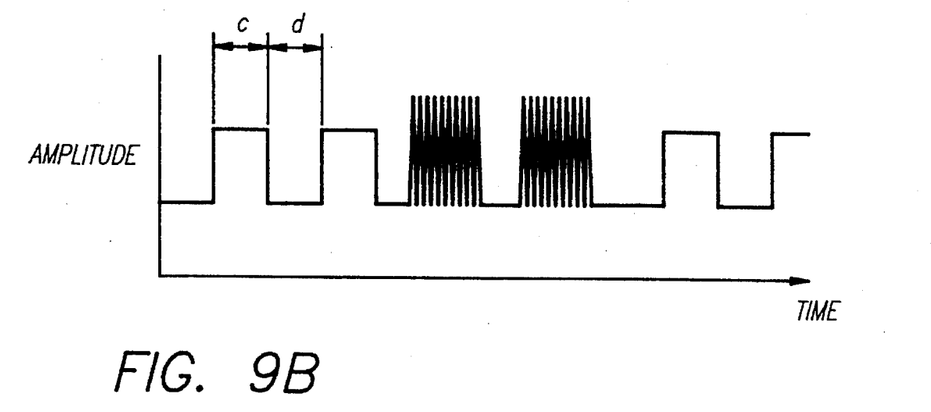

Once a desired rotational rate is achieved, an imaging operation of the catheter can then be conducted. As illustrated in FIG. 9B, low frequency pulses have a substantially reduced width (c) and spacing (d) are periodically interspersed with high frequency acoustic signals provided by the high frequency transducer 16. The high frequency acoustic signals pass through the turbine 30 and are either reflected or refracted from the turbine outward into the vessel.

The acoustic signals then travel through the body fluid within the vascular vessel until they encounter a change in acoustic impedance, which occurs when the emitted acoustic signals strike body tissue. The reflected acoustic signals then travel back following the same path to the high frequency transducer 16. The high frequency transducer 16 converts the reflected acoustic signals into corresponding electrical signals that contain information on the contours of the inside surface of the vessel. The use of a high frequency acoustic signal relative to the rotation rate of the turbine 30 ensures that image data for each angular position along the interior surface of the vessel can be obtained. The signals representing each angular position are collected, processed and displayed on a CRT screen as a two-dimensional, cross-sectional image.

Figure 9C:
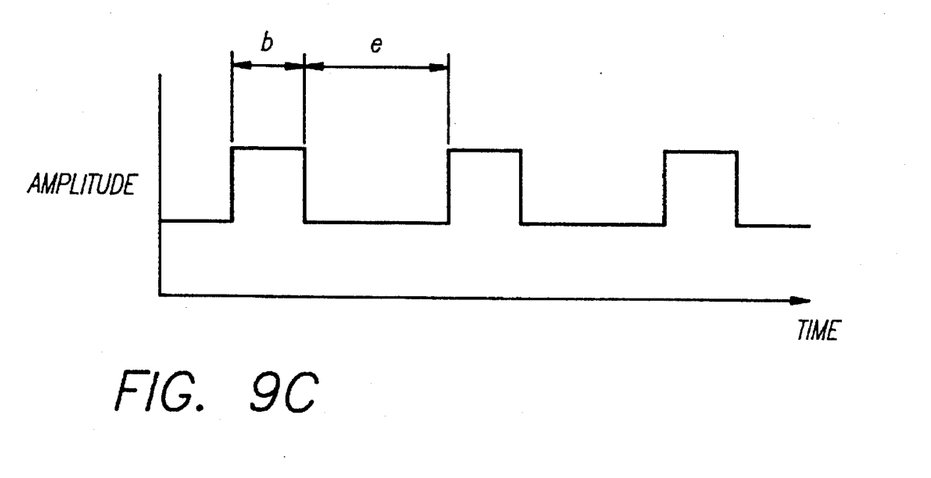

A third mode of operation of the turbine 30 is a speed maintenance mode, as illustrated at FIG. 9C. Low frequency acoustic pulses having a width (b) equivalent to that of the rotation initiation pulses of FIG. 9A are periodically provided to the turbine 30. These low frequency pulses maintain a desired rotation rate of the turbine 30. Since substantially less energy is required to maintain the desired rotation rate than to bring the turbine 30 up to operational speed from a non-rotating state due to the low friction environment of the turbine, a greater spacing (e) is provided between adjacent acoustic pulses. Once the low frequency acoustic pulses are discontinued, the turbine 30 will decelerate to a non-rotating state.

Figure 13:
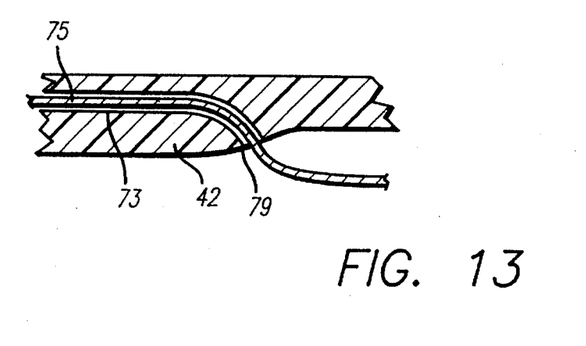
FIG. 13 is a partial side sectional view of the ultrasound diagnostic probe for use with a monorail guidewire.

Referring finally to FIG. 13, an alternative embodiment of the outer tubular element 42 is illustrated. As in FIGS. 2 and 5, a lumen 73 is provided to carry a guidewire 75. Instead of terminating the guidewire 75 at the point 77, a port 79 is provided enabling the guidewire to exit the lumen 73. In operation, the guidewire 75 may be initially threaded into the vessel. The exposed proximal end of the guidewire 75 external to the patient may then be inserted into the port 79, and through the lumen 73. As a result, the catheter may then slide along the pre-inserted guidewire 75 within the vessel. The acoustic waveguide 22 may be carrying acoustic signals to image the vessel as the catheter is being inserted. This type of guidewire system is referred to as a monorail guidewire. It should be apparent that the monorail guidewire of FIG. 13 can also be advantageously utilized in the catheters of FIGS. 2 and 5.

Having thus described a preferred embodiment of the ultrasound diagnostic probe having an acoustically driven turbine, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. A catheter apparatus for obtaining an image of internal surface characteristics of a vascular vessel, comprising:

a tubular element adapted for insertion into the vascular vessel;

a non-rotating acoustic waveguide disposed within said tubular element and coupled to a source of an ultrasonic signal located external to the vascular vessel; and means responsive to said ultrasonic signal for directing said ultrasonic signal in a rotating pattern from a distal end of said acoustic waveguide through a distal end of said tubular element.

2. The catheter apparatus of claim 1, wherein said directing means further comprises an acoustically driven turbine.

3. The catheter apparatus of claim 2, wherein said acoustically driven turbine comprises a plurality of turbine blades.

4. The catheter apparatus of claim 1, wherein said directing means further comprises an acoustic reflecting surface.

5. The catheter apparatus of claim 1, wherein said directing means further comprises an acoustic refracting layer.

6. The catheter apparatus of claim 1, wherein ultrasonic signal further comprises a low frequency ultrasonic signal and a high frequency ultrasonic signal, said low frequency ultrasonic signal cooperating with said directing means to direct said high frequency ultrasonic signal in said rotating pattern.

7. The catheter apparatus of claim 1, wherein said source of said ultrasonic signal further comprises at least one transducer.

8. The catheter apparatus of claim 1, further comprising a lumen provided in an inner portion of said tubular element capable of carrying a flexible guidewire.

9. The catheter apparatus of claim 8, further comprising a port disposed in said tubular element and coupled to said lumen, said port capable of carrying a monorail guidewire.

10. A catheter apparatus for obtaining an image of a vascular vessel comprising:

a tubular element adapted for insertion into the vascular vessel;

a non-rotating acoustic waveguide disposed within said tubular element coupled to a source of a high frequency ultrasonic signal and a low frequency ultrasonic signal located external to the vascular vessel; and a turbine responsive to said low frequency ultrasonic signal and disposed at a distal end of said acoustic waveguide, wherein rotation of said turbine directs said high frequency ultrasonic signal in a rotating pattern from said distal end of said acoustic waveguide through said tubular element.

11. The catheter apparatus of claim 10, wherein said high frequency ultrasonic signal is directed through said tubular element at an angle relative to an axis of said vascular vessel.

12. The catheter apparatus of claim 10, wherein said turbine comprises a plurality of turbine blades.

13. The catheter apparatus of claim 10, wherein said turbine further comprises an acoustic reflecting surface.

14. The catheter apparatus of claim 10, wherein said turbine further comprises an acoustic refracting layer.

15. The catheter apparatus of claim 10, wherein said source of said high frequency and said low frequency ultrasonic signals further comprises at least one transducer.

16. A method for imaging an interior surface of a vascular vessel comprising the steps of:

generating an ultrasonic signal using a transducer located external to the vascular vessel, said ultrasonic signal including a high frequency signal and a low frequency signal;

directing the ultrasonic signal into the vascular vessel through a non-rotating waveguide disposed within a catheter inserted into the vascular vessel;

driving a turbine by said low frequency signal to sweep the high frequency signal continuously in a predetermined pattern about the interior surface of the vascular vessel;

receiving the high frequency signal after reflection from the interior surface of the vascular vessel; and producing an image from the reflected signal.

17. The method as in claim 16, wherein the ultrasonic signal is directed through the non-rotating waveguide in a direction generally axial relative to the vascular vessel and is directed by said turbine in a transverse direction.

18. The method as in claim 17, wherein said turbine comprises a reflective surface.

19. The method as in claim 16, wherein the high frequency ultrasonic signal is directed at a forward angle from 10° to 90° relative to an axis of the vascular vessel.

20. The method as in claim 19, wherein said turbine comprises a refractive layer.

* * * * *